United States Patent [19]
Jones et al.

[11] Patent Number: 5,992,089
[45] Date of Patent: Nov. 30, 1999

[54] PROCESS FOR SEQUESTERING INTO THE OCEAN THE ATMOSPHERIC GREENHOUSE GAS CARBON DIOXIDE BY MEANS OF SUPPLEMENTING THE OCEAN WITH AMMONIA OR SALTS THEREOF

[76] Inventors: Ian S.F. Jones, P.O. Box 363, Glebe 2031; William Rodgers, 7/15 Clovelly Rd., Randwick, NSW, 2031; Michael Kassipillai Gunaratnam, 3 Kelley St., Marsfield, NSW, 2122; Helen Elizabeth Young, P.O. Box 748, Woollahra 2025, all of Australia

[21] Appl. No.: 08/515,280

[22] Filed: Aug. 15, 1995

[30] Foreign Application Priority Data

Dec. 16, 1994 [AU] Australia .................................. 660913

[51] Int. Cl.⁶ ........................... A01B 79/00; A01G 33/00; A01H 13/00; C12N 1/12
[52] U.S. Cl. .................................... 47/58.1; 47/1.4; 47/1.5
[58] Field of Search ................................ 47/1.4, 1.5, 58.1

[56] References Cited

U.S. PATENT DOCUMENTS

| | | | |
|---|---|---|---|
| 2,732,661 | 1/1956 | Spoehr | 47/1.4 |
| 2,908,113 | 10/1959 | Martin | 47/1.4 |
| 3,195,271 | 7/1965 | Golueke et al. | 47/1.4 |
| 3,650,068 | 3/1972 | Meyer et al. | 47/1.4 |
| 4,137,868 | 2/1979 | Pryor | 47/1.4 |

FOREIGN PATENT DOCUMENTS

| | | | |
|---|---|---|---|
| 2103462 | 4/1972 | France | 47/1.4 |

OTHER PUBLICATIONS

Thurman, 1978, "*Introductory Oceanography*", Second Edition, Charles E. Merrill Publishing Company, Columbus, Ohio, pp. 348–351.

Odum, 1971, "*Fundamentals of Ecology, Third Edition*", W.B. Saunders Company, Philadelphia, pp. 324–351.

The New Grolier Multimedia Encyclopedia, 1993, Release 6, topics "Oceanic Nutrients", "Fertilizer", "Pollution, Environmental", "Plankton", "Nutrient Cycles".

Grad, 1997, "Ocean nourishment could reduce greenhouse gases", Engineers Australia, May issue, pp. 34–35.

*Primary Examiner*—David T. Fox
*Assistant Examiner*—Anne Marie Grünberg
*Attorney, Agent, or Firm*—Ostrolenk, Faber, Gerb & Soffen, LLP

[57] ABSTRACT

The present invention provides a method for removing $CO_2$ from the atmosphere. The method comprises the step of delivering a source of nitrogen to the mixed layer of the ocean to cause an increase in the number of phytoplankton in the mixed layer and thereby increase the amount of photosynthesis carried out by the phytoplankton. The source of nitrogen is delivered to the mixed layer at a location where an ocean current will carry the source of nitrogen and phytoplankton over a region of the ocean having a depth sufficient to allow dead phytoplankton and organic material derived from the phytoplankton to fall from the mixed layer and enable carbon originating from the $CO_2$ to be sequestered from the atmosphere.

12 Claims, 2 Drawing Sheets

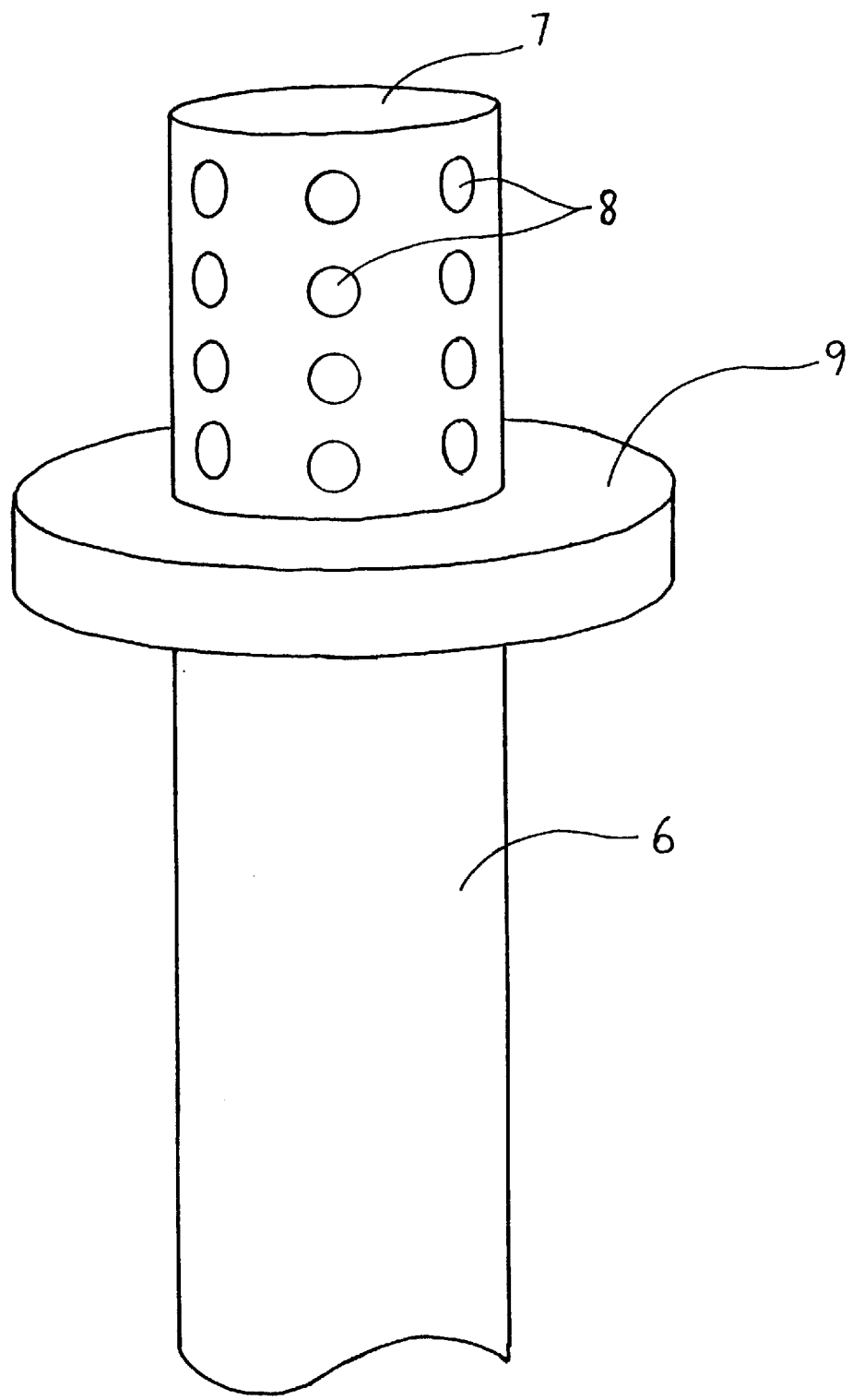

PROCESS FOR SEQUESTERING INTO THE OCEAN THE ATMOSPHERIC GREENHOUSE GAS CARBON DIOXIDE BY MEANS OF SUPPLEMENTING THE OCEAN WITH AMMONIA OR SALTS THEREOF

FIELD OF THE INVENTION

The present invention relates to a method for removing carbon dioxide from the atmosphere. More particularly, the method of the present invention involves delivering an exogenous source of nitrogen to a specific layer of the ocean at a specific location to stimulate the growth of the phytoplankton population in the specific layer and so cause an increase in the photosynthetic activity of the phytoplankton population.

BACKGROUND OF THE INVENTION

It is generally agreed under the United Nations Framework Convention on Climate Change (FCCC) that there is a need to reduce the $CO_2$ content of the atmosphere. The present invention may enhance the global environment by slowing potentially harmful changes to the climate due to increases in atmospheric $CO_2$, a so-called greenhouse gas. The method may allow $CO_2$ to be removed from the atmosphere for centuries and increase fish stocks for consumption by peoples of developing countries. Cost efficient fossil fuel may therefore be burnt while their by-product, $CO_2$, is put to use rather than dumped into the atmosphere.

The natural process by which carbon dioxide present in the ocean is sequestered is known. (Andersen, N. R. and A. Malahoff, 1977: The fate of fossil fuel $CO_2$ in the ocean. Plenum Press, N.Y., 749pp.). When atmospheric carbon dioxide dissolves in the ocean it exists in an ionic form and is taken into the bodies of marine phytoplankton through the process of photosynthesis. The phytoplankton eventually perish through age or are grazed by zooplankton. The resulting dead or excreted biomass then falls to lower levels of the water column where it is broken down by bacteria which re-release the carbon into the water column. However, typically 10% of the biomass escapes bacterial decomposition and falls to the ocean depths thereby effectively sequestering the carbon from the atmosphere.

It has been speculated that about 20% of ocean surface waters are deficient in trace nutrients required for phytoplankton growth. Martin et al (Nature, Vol. 371, pgs. 123–128) observed an increase in phytoplankton populations when iron was added to the sea surface in areas where phytoplankton numbers were low.

SUMMARY OF THE PRESENT INVENTION

In contrast to the above mentioned prior art the present invention teaches that phytoplankton populations can be increased by adding a source of nitrogen to the mixed layer of the ocean and that by delivering the source of nitrogen to a specific location of the ocean the phytoplankton population can be utilised to decrease the atmospheric $CO_2$ concentration.

In a first aspect of the present invention there is provided a method for removing $CO_2$ from the atmosphere comprising the step of delivering a source of nitrogen to the mixed layer of the ocean to cause an increase in the number of phytoplankton in the mixed layer and thereby increase the amount of photosynthesis carried out in the mixed layer by the phytoplankton, wherein the source of nitrogen is delivered to the mixed layer at a location where ocean currents will carry the source of nitrogen and phytoplankton to a region of the ocean having a depth sufficient to allow dead said phytoplankton and organic material derived from the phytoplankton to fall from the mixed layer and enable carbon from the $CO_2$ to be sequestered from the atmosphere.

As $CO_2$ present in the mixed layer of the ocean is used in photosynthesis carried out by the phytoplankton further $CO_2$ diffuses into the mixed layer from the atmosphere. Accordingly, the addition of the source of nitrogen to the mixed layer enhances the function of the ocean as a sink for carbon dioxide and results in a reduction in the carbon dioxide concentration in the atmosphere.

The phrase "source of nitrogen" will be understood to mean a nitrogen containing compound or compounds which can be used by the phytoplankton.

The phrase "mixed layer of the ocean" wherever used in the specification is to be taken to mean the upper layer of the ocean which is penetrated by sunlight and which is subject to mixing by the atmosphere.

The phrase "ocean currents" will be understood to include a current at the selected location of the ocean which is capable of directly carrying the source of nitrogen and phytoplankton to the region of the ocean. The phrase will also be understood to include situations where at least one or more currents at or in the vicinity of the selected location act to carry the nitrogen and phytoplankton to a second location where a prevailing current then moves the source of nitrogen and phytoplankton to the region of the ocean.

Typically, the mixed layer extends from the surface of the ocean to a depth of about 50 meters. However, the mixed layer may extend to a depth of 100 meters or more. The actual depth of the mixed layer varies and is dependent upon a number of factors including wind strength and the temperature difference between the oceanic surface waters and the lower atmosphere.

In embodiments of the present invention the source of nitrogen used is ammonia or one of its salts. While it is preferable that the ammonia is in solution, ammonia in the gas phase may also be utilised in the invention. Ammonia occurs naturally in sea water as a result of the bacterial decay of dead phytoplankton or zooplankton excretions.

However, other sources of nitrogen may be used in the present invention such as sodium nitrate and nitric acid.

In preferred embodiments the source of nitrogen is pumped into the mixed layer through a pipeline. Typically, the concentration of the source of nitrogen pumped into the mixed layer is such that the concentration of nitrogen in the vicinity of the pipeline outlet is raised between about 10 to 60 $\mu g$ per liter of seawater. The actual concentration of the source of nitrogen in the pipeline depends on the strength of the ocean current at the pipeline outlet.

Typically, the region of the ocean to which the ocean currents carry the source of nitrogen and phytoplankton is about 1000 meters deep or greater.

It is an advantage that a method embodied by the present invention causes the removal of $CO_2$ from the atmosphere and results in carbon from the $CO_2$ being locked away in the deep ocean from the atmosphere for significantly long periods of time.

By increasing phytoplankton numbers through the presence of the added source of nitrogen ocean fish stocks may be enhanced.

BRIEF DESCRIPTION OF THE DRAWINGS

The invention is described in greater detail hereinafter with reference to preferred, non-limiting embodiments illustrated in the accompanying drawings.

FIG. 2 is a perspective view of a diffuser.

DETAILED DESCRIPTION OF PREFERRED EMBODIMENTS OF THE INVENTION

Figure 1:
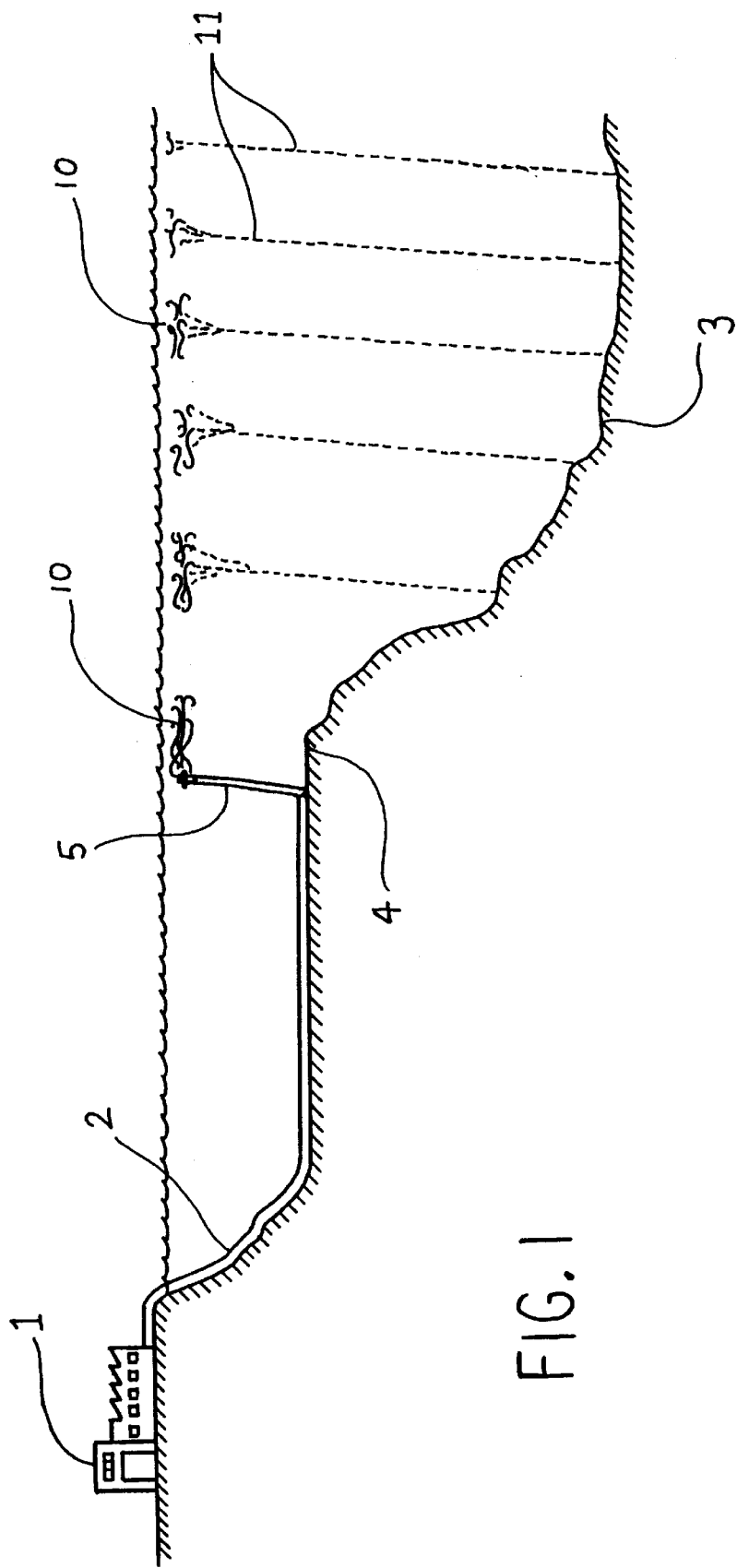
FIG. 1 is a schematic representation of a method embodied by the invention.

FIG. 1 illustrates a land based pumping station 1 for pumping ammonia in solution through a pipeline 2 into the mixed layer of the ocean at a selected location. An ocean current at the selected location carries the ammonia and phytoplankton consuming the ammonia to a region of the ocean characterised by having a sea-bed 3 at a depth of about 1000 meters or more. Preferably, sea-bed 3 is at a depth of at least 1500 meters.

Alternatively, the source of nitrogen may be pumped through a pipeline by a pump arranged in the pipeline itself. Moreover, the source of nitrogen may be supplied from land or from a platform anchored at sea.

Pipeline 2 may be up to 50 km, 100 km, 200 km or greater in length. The actual length of pipeline 2 depends on the distance of pumping station 1 from a suitable ocean current. Preferably, the outlet of the pipeline is located close to the edge of continental shelf 4. One example of a possible location for the outlet of the pipeline is off Smoky Cape, New South Wales, Australia (approx. latitude 30° S). However, there are of course other locations which are suitable for carrying out the present invention.

The ammonia solution is pumped through substantially vertical riser pipe 5 which extends into the mixed layer of the ocean. The addition of the ammonia to the mixed layer raises the concentration of nitrogen in the vicinity of the outlet of riser pipe 5 about 35 $\mu$g per liter of seawater. This concentration is below levels which occur sporadically in the upper ocean due to upwelling events.

Preferably, the ammonia solution is released into the mixed layer through a plurality of riser pipes 5 which may be spaced apart from each other by a distance of up to 1000 meters or more. The respective riser pipes 5 may also be arranged so that the ammonia solution is released into the mixed layer at different depths.

Each riser pipe 5 may be provided with a flexible joint allowing an upper section of the pipe to move in the unlikely event of being inadvertently struck by a passing vessel.

Preferably, a diffuser 6 is connected to the upper end of riser pipe 5 to facilitate the dispersion of the ammonia into the mixed layer. One example of a suitable diffuser 6 is illustrated in FIG. 2. Diffuser 6 consists of a tubular member having a sealed end 7 and a plurality of holes 8 through which the ammonia exits into the mixed layer. The ammonia enters diffuser 6 through an opposite end which is connected to riser pipe 5.

Flotation devices may be connected to diffuser 6 or to the upper end section of the riser pipe 5 to maintain riser pipe 5 substantially vertical. For example, diffuser 6 illustrated in FIG. 2 is provided with a flotation collar 9. However, it will be appreciated by the skilled addressee that it is not necessary that riser pipe 5 be held in a substantially vertical position.

As depicted in FIG. 1 the ammonia is released into the mixed layer away from immediate contact with the atmosphere. Typically, the ammonia solution is released at a depth of about 35 meters.

However, ammonia may be added to the mixed layer by bubbling gaseous ammonia from an outlet located beneath the mixed layer of the ocean. Alternatively, ammonia in solution may be sprinkled onto the mixed layer from an outlet positioned above the surface of the ocean.

The released ammonia forms a nutrient plume 10 which is transported by the ocean current over sea-bed 3. Eddy currents and diffusion assist in the dispersion of the ammonia through the mixed layer.

The presence of the added ammonia together with sunlight enable the phytoplankton in the mixed layer to multiply as the ammonia is consumed. Dead phytoplankton and organic material comprising excretion from zooplankton subsequently fall to lower levels of the water column as organic detritus 11 as the ocean current carries the ammonia and phytoplankton over sea-bed 3.

The organic detritus 11 carries with it carbon originating from $CO_2$ from the atmosphere enabling effective sequestering of the carbon to deeper ocean layers or sea-bed 3.

Although the present invention has been described hereinbefore with reference to several embodiments, numerous variants and modifications are possible without departing from the scope of the invention which is defined in the following claims.

We claim:

1. A method for removing carbon from oceanic water comprising the steps of:
   locating a first region of the ocean at a distance from the shore where ocean currents are sufficient to carry a nitrogen source delivered to the first region along with phytoplankton to and over a second region of the ocean having a depth sufficient to allow dead phytoplankton and organic material derived therefrom to fall;
   supplying multiple sources of reactive nitrogen to the mixed layer of the ocean in the first region, wherein the multiple sources are spaced apart from each other over a distance across the first region and wherein each reactive nitrogen source is of a concentration sufficient to raise the concentration of nitrogen in the vicinity of each source in the range of 10 to 60 micrograms of reactive nitrogen per liter of ocean water.

2. A method according to claim 1 wherein the source of nitrogen is ammonia or a salt thereof.

3. The method of claim 1, wherein the concentration of nitrogen in the vicinity of each source of reactive nitrogen is raised by approximately 35 micrograms of reactive nitrogen per liter of ocean water.

4. The method of claim 1, wherein the sources of nitrogen comprise delivering the reactive nitrogen through multiple spaced apart outlets each corresponding to one of the sources of the reactive nitrogen in the first region.

5. The method of claim 4, wherein the delivering of the reactive nitrogen comprises providing a pipeline extending into the first region of the ocean, wherein the pipeline includes the multiple outlets in the first region and within the mixed layer of the ocean, the mixed layer being the upper layer of the ocean which is penetrated by some light and subject to mixing by the atmosphere, the outlets being spaced a distance apart within the first region for delivering the reactive nitrogen to a plurality of locations over the first region.

6. The method of claim 5, wherein the reactive nitrogen is delivered to the multiple outlets at the same time.

7. The method of claim 5, wherein the pipeline outlets are positioned near the continental shelf.

8. The method of claim 1, wherein the first region is located to be where ocean currents are expected to carry the reactive nitrogen toward the second region of the ocean having a sea bed of over 1,000 m in depth.

9. The method of claim 1, wherein the supplying of the reactive nitrogen to the mixed layer is below the surface of the ocean in the first region.

10. The method of claim 1, wherein the reactive nitrogen sources are spaced from each other in the first region by distances of up to 1,000 meters.

11. The method of claim 1, wherein the reactive nitrogen sources are spaced from each other in the first region by distances over 1,000 meters.

12. The method of claim 1, wherein the sources of reactive nitrogen are selected from the group consisting of ammonia, an ammonia salt, sodium nitrate and nitric acid.

* * * * *